(12) United States Patent  
Kumar (10) Patent No.: US 7,278,430 B2
(45) Date of Patent: Oct. 9, 2007

(54) BLOOD VESSEL OCCLUSION DEVICE (75) Inventor: Ravi Kumar, Briarcliff Manor, NY (US)

(73) Assignee: Arvik Enterprises, LLC, Dobbs Ferry, NY (US)

( * ) Notice: Subject to any disclaimer, the term of this patent is extended or adjusted under 35 U.S.C. 154(b) by 793 days.

(21) Appl. No.: 10/086,753

(22) Filed: Mar. 1, 2002

(65) Prior Publication Data
US 2003/0167065 A1 Sep. 4, 2003

(51) Int. Cl.
A61B 17/00 (2006.01)
(52) U.S. Cl. .................................................... 128/887
(58) Field of Classification Search ................ 606/200, 606/194, 157, 158, 191, 213; 604/907; 128/887, 831, 843; 623/1.1
See application file for complete search history.

(56) References Cited

U.S. PATENT DOCUMENTS

| 3,626,947 | A |   | 12/1971 | Sparks | 128/334 |
|---|---|---|---|---|---|
| 3,958,557 | A |   | 5/1976 | Sharp et al. | 128/1 |
| 4,710,192 | A | * | 12/1987 | Liotta et al. | 606/108 |
| 4,852,568 | A |   | 8/1989 | Kensey | 128/325 |
| 5,042,161 | A |   | 8/1991 | Hodge | 33/501.45 |
| 5,171,270 | A | * | 12/1992 | Herrick | 623/11.11 |
| 5,334,137 | A | * | 8/1994 | Freeman | 604/8 |
| 5,382,261 | A | * | 1/1995 | Palmaz | 606/158 |
| 5,425,757 | A |   | 6/1995 | Tiefenbrun et al. | 623/2 |
| 5,527,338 | A | * | 6/1996 | Purdy | 606/200 |
| 5,645,565 | A |   | 7/1997 | Rudd et al. | 606/213 |
| 5,656,036 | A |   | 8/1997 | Palmaz | 623/12 |
| 5,725,551 | A |   | 3/1998 | Myers et al. | 606/213 |
| 5,728,133 | A |   | 3/1998 | Kontos | 606/213 |
| 5,733,329 | A |   | 3/1998 | Wallace et al. | 623/1 |
| 5,755,779 | A |   | 5/1998 | Horiguchi | 623/1 |
| 5,826,587 | A |   | 10/1998 | Berenstein et al. | 128/898 |
| 5,843,164 | A | * | 12/1998 | Frantzen et al. | 623/1.16 |
| 5,879,366 | A |   | 3/1999 | Shaw et al. | 606/213 |
| 5,925,060 | A |   | 7/1999 | Forber | 606/191 |
| 5,928,266 | A |   | 7/1999 | Kontos | 606/213 |
| 5,944,750 | A |   | 8/1999 | Tanner et al. | 623/1 |
| 6,010,517 | A |   | 1/2000 | Baccaro | 606/151 |
| 6,016,806 | A | * | 1/2000 | Webb | 128/846 |
| 6,041,785 | A | * | 3/2000 | Webb | 128/887 |
| 6,082,362 | A | * | 7/2000 | Webb | 128/846 |
| 6,146,396 | A | * | 11/2000 | Konya et al. | 606/159 |
| 6,179,857 | B1 |   | 1/2001 | Diaz et al. | 606/194 |
| 6,248,112 | B1 |   | 6/2001 | Gambale et al. | 606/108 |
| 6,270,515 | B1 | * | 8/2001 | Linden et al. | 606/213 |
| 6,286,510 | B1 | * | 9/2001 | Ray et al. | 128/830 |
| 6,315,787 | B1 |   | 11/2001 | Tsugita et al. | 606/213 |
| 6,346,102 | B1 | * | 2/2002 | Harrington et al. | 606/28 |
| 6,458,092 | B1 |   | 10/2002 | Gambale et al. | 604/22 |
| 6,547,804 | B2 | * | 4/2003 | Porter et al. | 606/195 |
| 6,579,311 | B1 |   | 6/2003 | Makower | 623/1.23 |

(Continued)

Primary Examiner—(Jackie) Tan-Uyen T. Ho
(74) Attorney, Agent, or Firm—Gordon & Jacobson, PC (57) ABSTRACT A blood vessel occluding device including a plug and an insertion means to permanently occlude a blood vessel. In one embodiment, the plug has a tapered shape and is made of a biocompatible material such as Silicone. The plug is inserted axially into the blood vessel and is gripped firmly by the walls of the blood vessel. The insertion device is a spring loaded device that has a spring activated needle; this insertion device provides the axial force to insert the plug into the blood vessel. The blood vessel occluding device allows the blood vessel to be occluded quickly and effectively.

21 Claims, 5 Drawing Sheets

U.S. PATENT DOCUMENTS 6,629,533 B1 * 10/2003 Webb et al. .................. 128/887
6,638,293 B1 * 10/2003 Makower et al. ........... 606/200
6,746,468 B1 * 6/2004 Sepetka et al. .............. 606/200
7,017,580 B2 * 3/2006 Prescott et al. .............. 128/846

* cited by examiner

BLOOD VESSEL OCCLUSION DEVICE

BACKGROUND

The present invention relates to medical devices that are implanted in the human body. In particular, the present invention relates to medical devices that can be used to occlude blood vessels on a temporary or permanent basis.

Various implantable medical devices have been developed for treating ailments of the human body. One such implantable medical device is an occlusion device used to occlude blood vessels i.e. to prevent the flow of blood through these vessels. These occlusion devices may be used to occlude blood vessels either temporarily or permanently. In certain cases, for example, during a surgery, these devices may be used to stem the flow of blood while the surgery is performed. In other cases, such as in treatment of certain cardiovascular diseases, permanent occlusion devices may be used.

There are numerous situations where certain blood vessels such as arteries and veins may have to be occluded. Surgical treatment of an aneurysm is one such situation where occlusion devices are required. An aneurysm is a balloon-like swelling of a blood vessel such as an artery. This swelling may be caused due to diseases such as arteriosclerosis or cystic medial necrosis, or due to infections such as syphilitic or mycotic infections, or even due to trauma. Typically, the aneurysm results in a weakening of the wall of the artery or other blood vessel in which it occurs. The region of the artery (or the blood vessel) that has been affected by the aneurysm may tear or rupture over time because of sustained blood pressure. If the artery tears or ruptures, and consequently bleeding occurs, then there may be severe consequences for the patient. For instance, if an aneurysm affected artery in the brain bursts due to a weakened wall, then cranial hemorrhaging and subsequently even death may occur. Hence, aneurysms occurring in certain regions of the body may lead to life-threatening conditions and therefore need to be detected early and treated suitably.

Although an aneurysm may occur in any location of the human body, it is more likely to occur in the abdominal aorta. This type of aneurysm is referred to as an Abdominal Aortic Aneurysm (AAA). An AAA usually results in a large swelling in the affected region of the aorta. In cases where the aneurysm affected region of the aorta exceeds 6 cm in diameter, surgery may be necessary to treat the aneurysm.

In a typical surgery to treat a patient suffering from an AAA, an incision is made in the abdominal wall of the patient to expose the artery. In the next step, the portion of the aorta that is just above the aneurysm-affected region is clamped (so as to disallow any flow of blood) and then the affected portion of the abdominal aorta cut and opened.

Note that once the affected portion of the aorta has been opened, the blood vessels that originate from this cut region of aorta are exposed and begin to bleed profusely. Hence, in such cases it is necessary to seal these cut blood vessels to prevent excessive loss of blood. In such cases, occluding means are often employed during the surgery to prevent excessive bleeding from such blood vessels.

Three techniques are usually employed to occlude blood vessels. These include sealing of a blood vessel using a finger, sealing of the blood vessel using a clamp or a clip and suturing of the blood vessel.

In the first technique that is the simplest, a surgeon or other person assisting in the surgery seals the cut blood vessel using a finger. This technique is usually used since the finger may be readily applied to seal the cut blood vessel. However, this method is usually not suitable due to certain drawbacks. Firstly, the space available in the site of the surgery may be reduced considerably. Secondly, the hand of the person may not allow the blood vessel to be clearly seen and operated upon, and hence this technique may hinder access to the site of the surgery. Thirdly, this technique is not a permanent sealing arrangement. Because of these drawbacks, this technique is rarely used to occlude the affected blood vessels (for the entire duration of the surgery). Instead, this technique is sometimes used while another occluding mean is applied to the blood vessel.

In an alternative technique, a clamp or a clip may be used to occlude a blood vessel. In this technique, the clamp or clip is used to constrict the blood vessel so as to minimize blood flow through the narrow opening in the blood vessel. The surgical clamps and "ligating" clips come in a variety of shapes and sizes. In a typical design, a surgical clamp is connected to an elongated arm and is controlled with a handle. The elongated arm allows the surgeon to apply and remove the clamp easily during the surgery. Two such surgical clamps have been disclosed in U.S. Pat. Nos. 5,133,724 and 5,447,515. However, such designs are not always suitable since the long arm or handle may hinder the surgeon's access to the affected blood vessel.

Alternative designs of clamps also exist where the handle or other such clamp applier may be readily removed from the site of the surgery. U.S. Pat. No. 5,282,812 discloses one such clamp. However, such a surgical clamp has the drawback that it is difficult to quickly loosen or remove the clamp. In this method, the difficulty arises since the surgeon must apply the appropriate amount of force by hand for loosening and removing the clamp. Another drawback of these occlusion devices is that these may not be effective in completely sealing certain blood vessels. For instance, a blood vessel such as an artery usually has a very thick wall. Therefore, it may not be possible to completely seal such an artery using a clamp or a clip. Furthermore, the clamps may slip and slide out of position if a sufficiently large clamping force is not applied. However, this large clamping force may permanently damage the wall of the artery. Finally, the use of ligating clips and clamps is a temporary arrangement because it does not seem feasible to leave a metallic clamp inside a human body for a long duration. Thus, clamps and clips may not always be suitable for occluding blood vessels.

A third technique to occlude blood vessels is to suture these vessels. This technique allows the blood vessel to be completely sealed. However, suturing is usually a time-consuming procedure as compared to other methods mentioned above. Consequently, suturing may not be suitable for all surgical procedures. For instance, consider the surgical procedure used to treat an aneurysm in the lumbar region of the body. In this surgical procedure, a large number of blood vessels may need to be cut in order to treat the aneurysm. Hence, if the cut vessels are sutured, as is done currently, then there may be considerable loss of blood before all blood vessels have been occluded. Moreover, there may be difficulties in the suturing process itself if there are calcium deposits in the area of the aneurysm. Calcium deposits are likely to occur in this region since aneurysms usually begin as micro tears in the wall of the blood vessel, and calcium and other blood coagulating material are likely to deposit at the site of these tears. Furthermore, these calcium deposits may also weaken sutures that have been applied thereby decreasing the effectiveness of this technique.

Consequently, there is a need to quickly and effectively occlude blood vessels during surgical procedures. It should be noted that the need for occluding blood vessels occurs not only in surgery for treating aneurysms but also in other surgeries. Therefore, what is required is a sealing device capable of permanently occluding a variety of blood vessels in different regions of the body.

SUMMARY

It is an object of the present invention to provide a means to occlude a blood vessel such as an artery.

In order to attain the aforementioned object, the present invention provides a plug made of biocompatible material and an insertion syringe to allow the plug to be inserted into the blood vessel. The present invention allows for the blood vessel to be rapidly occluded. Furthermore, the plug may be used to permanently seal the blood vessel, and may be implanted in the body for long durations, even for the entire life of a patient.

It is a further object of the present invention to provide a means to effectively occlude a blood vessel such as an artery. Accordingly, the plug of the present invention is designed to be effective even in cases of deposits, such as calcium and/or cholesterol deposits, in the artery.

In a preferred embodiment of the present invention, a plug having a tapered shape is provided. The taper of the plug facilitates insertion of this plug into the blood vessel.

In an alternative embodiment of the present invention, a plug having an essentially cylindrical shape is provided. The cylindrical shape of the plug helps to secure the plug in the blood vessel, thereby effectively occluding the blood vessel.

In another alternative embodiment of the present invention, a plug having an umbrella shape is provided. This plug is particularly advantageous in occluding a blood vessel having calcium and other such deposits near opening of the blood vessel.

BRIEF DESCRIPTION OF THE DRAWINGS

The preferred embodiments of the invention will hereinafter be described in conjunction with the appended drawings provided to illustrate and not to limit the invention, wherein like designations denote like elements, and in which.

DESCRIPTION OF PREFERRED EMBODIMENTS

An Abdominal Aortic Aneurysm (AAA) is a disease that weakens the walls of the aorta and leads to swelling of the aneurysm affected region of the aorta. The weakened walls of the aorta may not be able to withstand the pressure of blood flowing through the aorta, and in extreme cases, the aorta may rupture in the affected region leading to internal hemorrhaging.

In most cases, surgery is required to treat the AAA. The treatment typically provides an alternate path for the flow of blood so as to bypass the aneurysm affected region of the aorta. Typically, the bypass is a graft that replaces the affected portion of the aorta.

In this surgery, a surgeon makes an incision in the abdominal wall of the patient and gains access to the aneurysm affected region of the aorta. Then, the surgeon clamps the aorta above and below the aneurysm affected region in order to block the flow of blood through the aorta. In the next step, the surgeon opens the aneurysm affected region of the aorta and provides an alternate path for the flow of blood. Thereby, the affected region is bypassed.

During the course of this surgery, the surgeon also occludes arteries that originate in this affected portion of the aorta; these arteries would otherwise bleed since these are part of a collateral circulation system. In a collateral circulation system, two or more arteries are interconnected by multiple smaller arteries and/or capillaries. Such an interconnected network of arteries leads to sufficient redundancy in the network. Therefore, if one of these arteries is blocked or damaged or otherwise rendered ineffective, blood is still supplied to regions of the body. However, this redundancy in the circulation system also leads to problems when one of these arteries is cut. For instance, the cut artery may start to bleed since the exposed artery would draw blood from the collateral circulation system. Consequently, arteries that are cut during this surgical procedure need to be quickly and effectively sealed.

In this surgery, opening of the aneurysm affected region of the aorta exposes 4 to 6 collateral arteries that originate in this region. The surgeon must occlude these 4 to 6 arteries. Currently, sutures are used to occlude these arteries. However, this procedure is time consuming and leads to significant loss of blood before all the arteries have been occluded. Furthermore, sutures may not be effective if there are calcium deposits in this region. And, it may also lead to an overall increase in the time of the surgical operation.

The present invention provides a plug 102 that may be used to quickly and effectively seal these arteries. In the recommended surgical procedure, the surgeon clamps the aorta above the aneurysm affected region. In the next step, the surgeon cuts open the aorta along its length so as to expose the aneurysm affected region of the aorta. This also exposes the collateral arteries originating in this region. Next, the surgeon uses plug 102 to quickly seal these arteries thereby preventing excessive loss of blood. Then, the surgeon prepares a graft so as to create an alternate path for the flow of blood. Hence, the aneurysm affected region of the aorta is bypassed.

Figure 1:
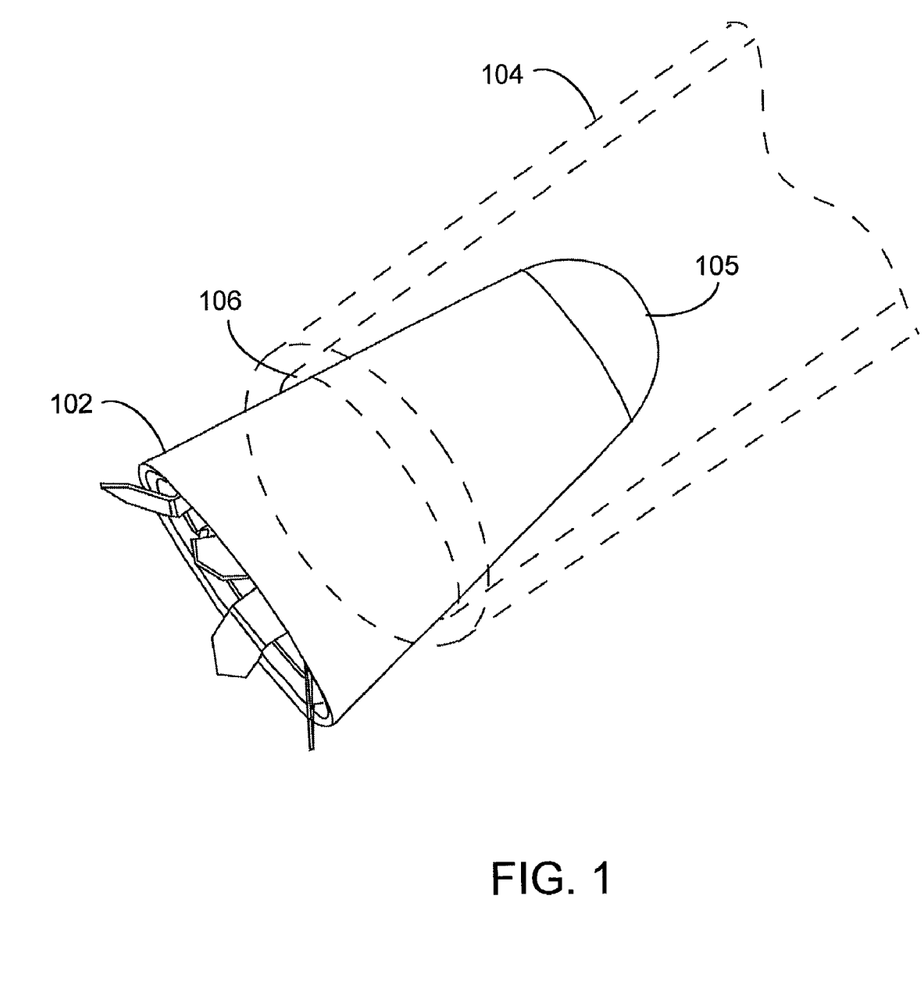
FIG. 1 shows an occlusion device inserted in a blood vessel in accordance with the present invention.

FIG. 1 illustrates an artery 104 that has been occluded using a plug 102 in accordance with the present invention. Artery 104 has a lumen 106 through which the blood flows and plug 102 has been inserted axially into lumen 106 to occlude artery 104. Plug 102 is axially symmetric and is inserted into artery 104 such that the axis of symmetry of plug 102 coincides with the longitudinal axis of artery 104. Further, plug 102 has a tapered shape; the diameter of rounded end 105 of plug 102 is smaller than lumen 106 and the diameter of the other end is larger than the diameter of lumen 106. This facilitates insertion of plug 102 into artery 104.

Artery 104 has a thick elastic wall surrounding lumen 106. This thick wall has been provided so as to withstand flow of blood at high pressure through artery 104. The elastic nature of artery 104 allows plug 102 to be tightly grasped by artery 104. Therefore, the elastic nature of the walls enables the plug to be effective in occluding artery 104. Furthermore, the elastic walls of artery 104 also permit a small range of plugs 102 to be used for different sizes of arteries 104. Thus, plug 102 of a certain size may be used for occluding arteries of different sizes. Typically, plug 102 ranges from 1 mm to 4 mm in diameter.

In the preferred embodiment, plug 102 is made of silicone, which is a popular material for making devices that are implanted inside the body for long durations. Silicone is useful since it is non-toxic, chemically inert, substantially insoluble in blood and substantially non-immunogenic. In addition to silicone, newer elastomeric biocompatible materials may also be used to manufacture plug 102. Ongoing research and development in biocompatible materials have created materials with a longer life, better strength and lower cost—all of which are desirable qualities of the material of plug 102. Typical examples of such materials include polyurethanes and polyisobutylene-based polymers.

Figure 2:
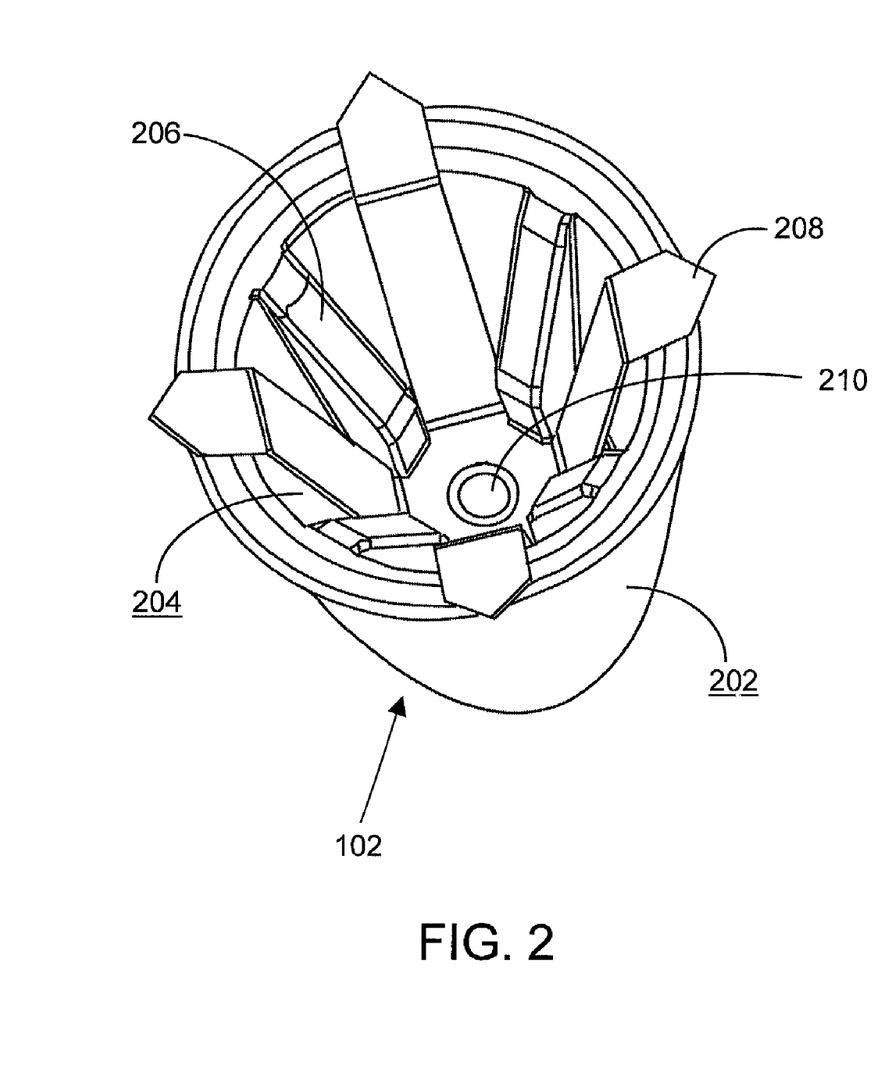
FIG. 2 shows the preferred embodiment of the occlusion device.

FIG. 2 shows internal construction of plug 102. Plug 102 is axially symmetric and substantially hollow. Plug 102 has an outer surface 202 having a tapered shape and an inner surface 204. The plug is made of sufficient strength to withstand forces acting on it. On inserting this plug into artery 104, the elastic walls of the artery exert a compressive force on plug 102. Furthermore, the plug is also subject to an axial force due to pressure of blood in the artery. Hence, in a preferred embodiment, inner surface 104 of plug 102 is corrugated and projections 206 are provided to add strength to plug 102. Further, plug 102 may be reinforced by means of spokes 208 attached to the inner surface 204. These spokes 208 are typically made of Tungsten or some other material of sufficient rigidity and strength. In addition, plug 102 has a pilot hole 210. This pilot hole 210 enables plug 102 to be mounted on insertion syringe 300, shown in FIG. 3.

In an alternative embodiment, plug 102 may be constructed without any reinforcing spokes 208. In this embodiment, plug 102 may be manufactured using materials of sufficient structural rigidity and strength. Furthermore, reinforcing spokes may be avoided by suitably increasing the thickness of plug 102.

In a typical surgery, plug 102 is inserted into artery 104 by positioning this plug axially over artery 104, and by applying an axial force. The surgeon may apply this force either by hand (if feasible) or by using an insertion device such as insertion syringe 300, shown in FIG. 3. This insertion syringe has a casing 302 and a lever 306; the surgeon uses lever 306 to operate insertion syringe 300. Lever 306 in turn enables a needle 308, housed in a tubular needle guard 310, to be pushed outwards. To insert the plug, the surgeon mounts plug 102 on the needle guard 310 of the insertion syringe. This is done by positioning needle guard 310 such that it fits snugly into pilot hole 210 of plug 102. Next, the surgeon aligns artery 104 and plug 102, and uses lever 306 to provide an axial force on needle 308 to insert plug 102 into artery 104. This force inserts plug 102 into artery 104; the artery has a smaller diameter than that of plug 102; further, the elastic walls of artery 104 tightly grip and secure plug 102.

Figure 4:
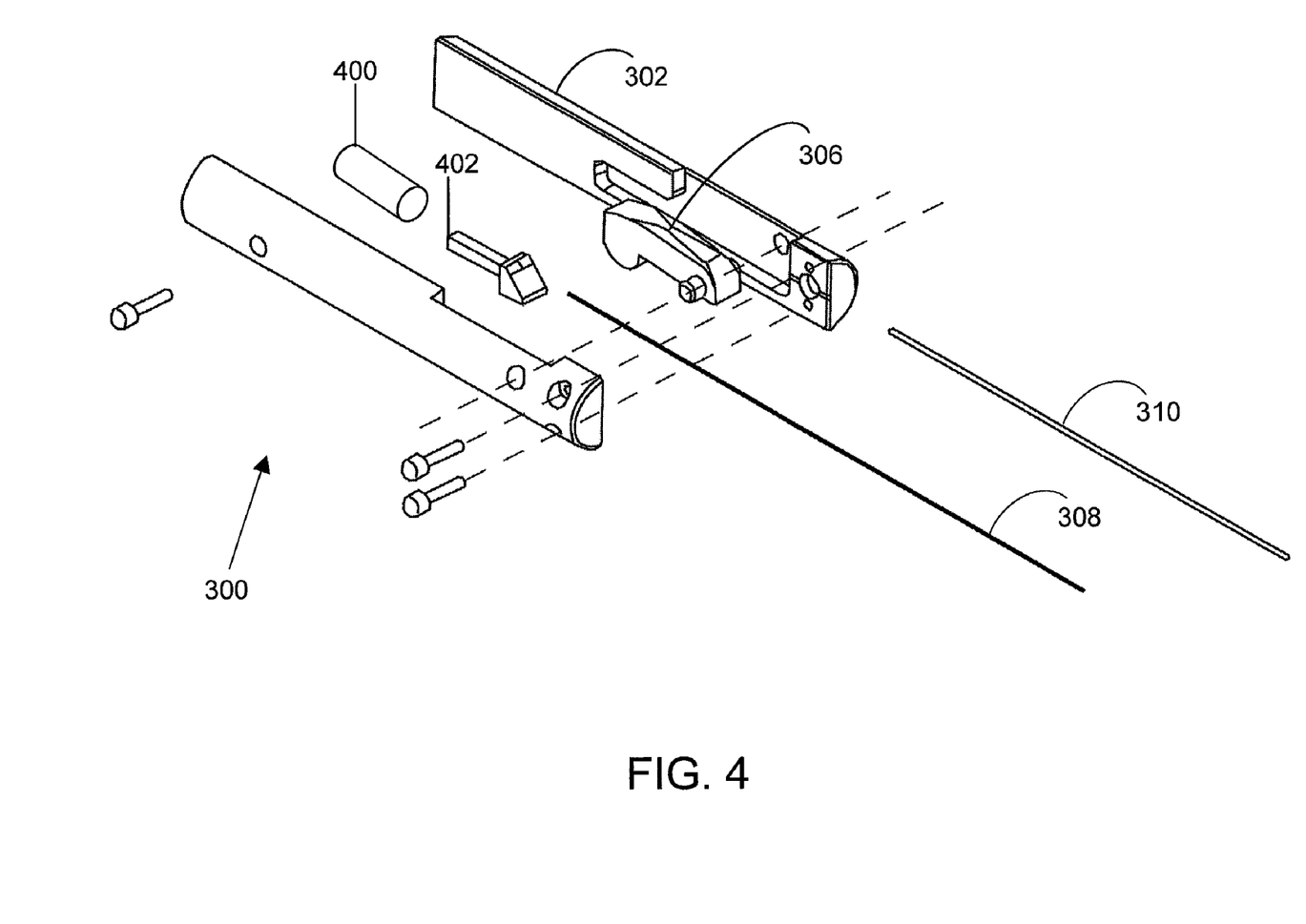
FIG. 4 shows an exploded view of the insertion syringe.

FIG. 4 shows an exploded view of insertion syringe 300. This syringe is essentially a spring activated device. A spring 400 and a needle guide 402 have been shown encased in casing 302. This spring is in a compressed state before lever 306 is activated, and needle 308 is pulled inside needle guard 310. Once lever 306 is activated, spring 400 unwinds and propels needle guide 402; in turn, this needle guide propels needle 308 outwards. Hence, plug 102 that is attached to needle guard 310 is propelled outwards and inserted into artery 104.

Figure 3:
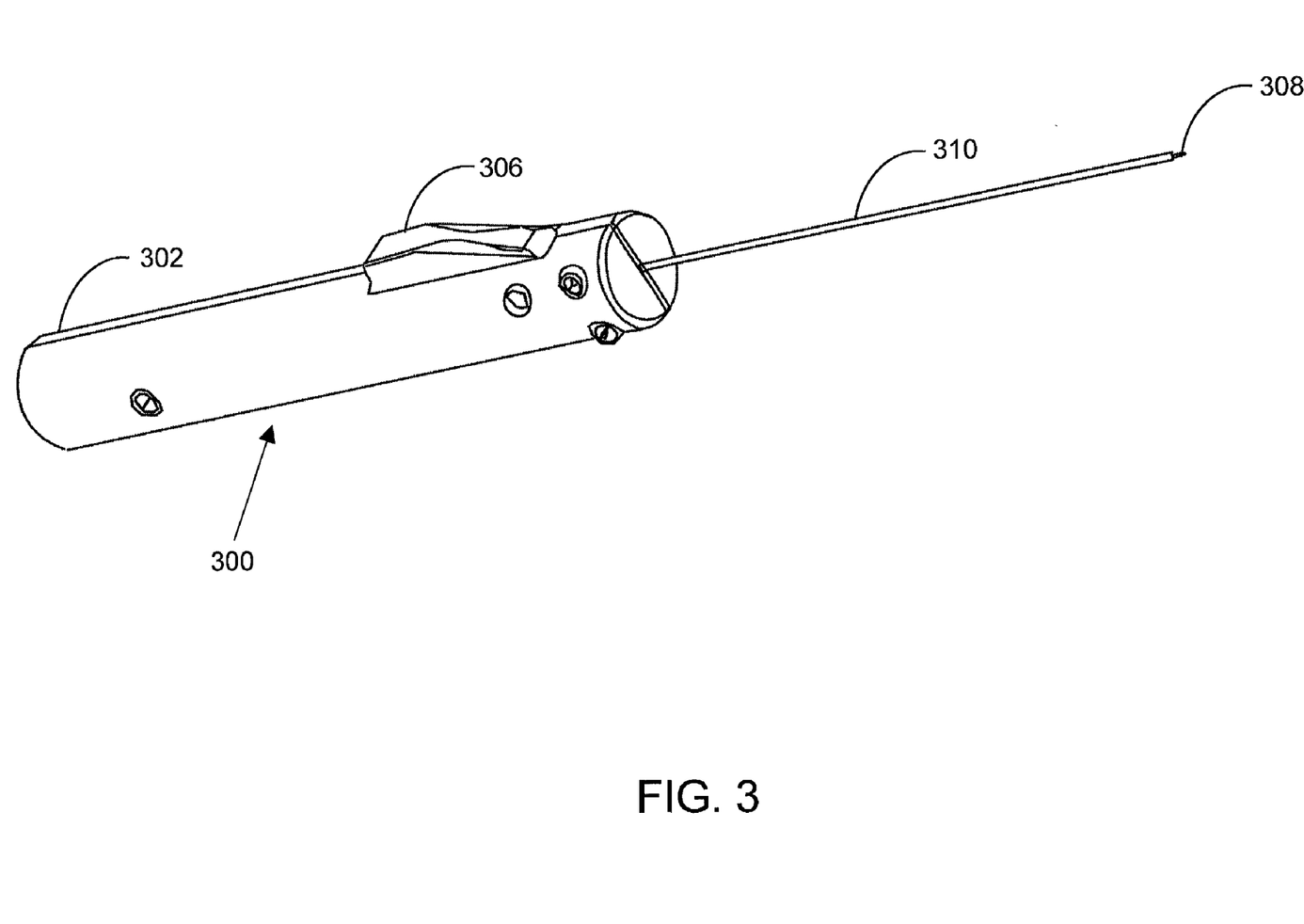
FIG. 3 shows an insertion syringe in accordance with the present invention.

It will be apparent to one skilled in the art that alternative ways to propel the needle may be employed in insertion syringe 300. For instance, needle 308 of insertion syringe 300 could be propelled outwards using air or other fluid means at high pressure.

Figure 5:
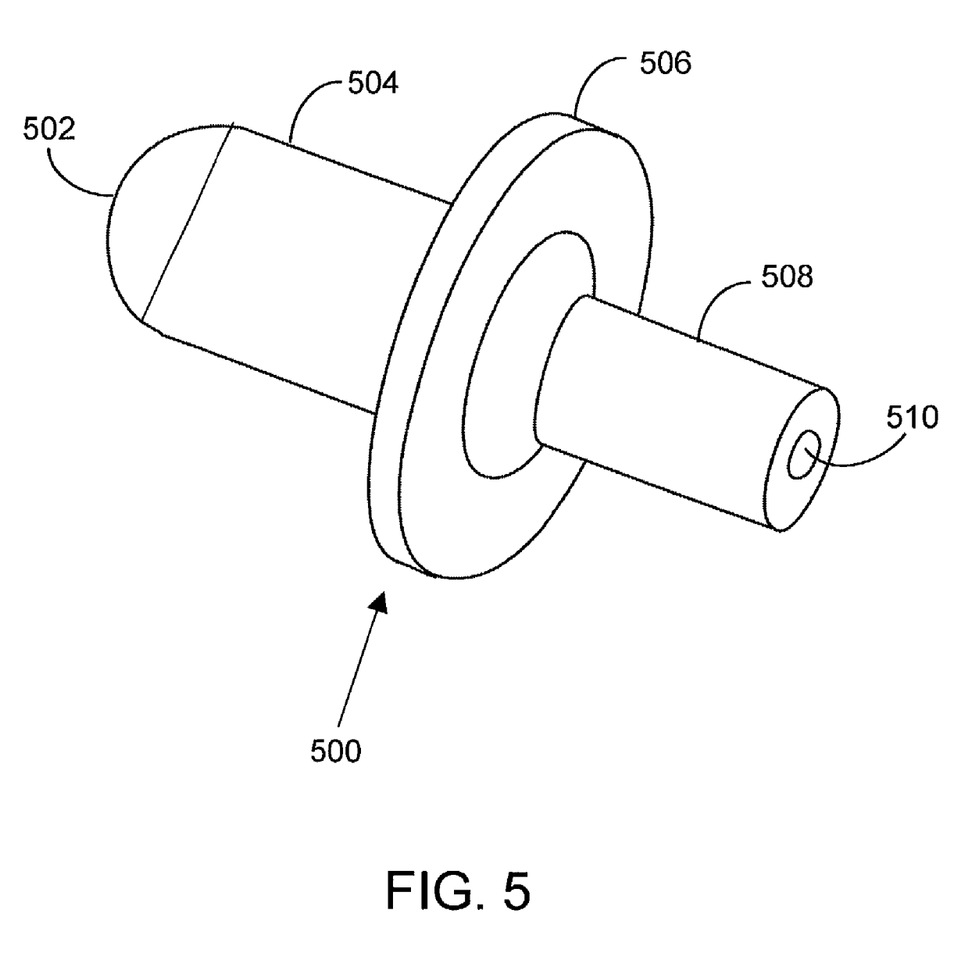
FIG. 5 shows an alternate embodiment of the occlusion device.

FIG. 5 shows an alternative embodiment 500 of the present invention used to occlude an artery 104. Plug 500 is also symmetric about its axis. Further, plug 500 has a rounded end 502 that facilitates introduction of plug 500 into artery 104. On inserting this plug, elastic walls of artery 104 wrap around end 502 and tubular section 504 of plug 500. In this plug, diameter of rounded end 502 and diameter of tubular section 504 are slightly larger than diameter of lumen 106 of artery 104. Consequently, artery 104 tightly grips plug 500 and plug 500 effectively occludes the artery. This tubular section 504 is followed by a disc 506 having a larger diameter than that of tubular section 504. Upon inserting this plug, rounded end 502 and tubular section 504 enter the artery whereby the artery wraps around tubular section 504 along its length up to disc 506. Following disc 506 is another tubular section 508 having a pilot hole 510. Pilot hole 510 allows plug 500 to be used in conjunction with insertion syringe 300 thereby enabling plug 500 to be quickly applied to occlude artery 104. Plug 500 is also made of a biocompatible material such as Silicone.

In another alternative embodiment, a plug shaped like an umbrella is used to occlude artery 104. This plug is also axially symmetric. This plug exists in two configurations—a compressed state and an expanded state. This plug comprises an elastic outer surface and a plurality of ribs connected to this outer surface. These ribs may be operated to transform the plug from the compressed state to the expanded state. The umbrella shaped plug is introduced into artery 104 in the compressed state. In this state, the plug has a diameter less than the diameter of lumen 106. Thereafter, the surgeon uses insertion syringe 300 to operate the ribs, whereby the outer surface expands to occlude artery 104. The plug preferably uses a two cylinder mechanism to achieve this expansion. In this mechanism, a first cylinder is connected to the insertion syringe, and a second cylinder is connected to the ribs. In operating this mechanism, the second cylinder slides over the first cylinder to operate the ribs, thereby causing the plug to expand and occlude the artery 104. This plug is particularly advantageous in occluding an artery with calcium and other deposits near the opening of the artery. These deposits may not allow plugs to be effectively gripped by the artery. However, this umbrella shaped plug may be applied at a location where such deposits are absent, thereby effectively occluding the artery.

While the present invention has been discussed in connection with surgical repair of an aneurysm, it will be apparent to those skilled in the art that it may also be applied in other surgical procedures. For instance, the plugs of the present invention may be used to occlude arteries in other regions of the body. Furthermore, these plugs may also be used to occlude other blood vessels such as veins and capillaries. The plugs may be utilized in permanent or temporary procedures.

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention as described in the claims.

What is claimed is:

1. An apparatus for occluding a blood vessel having a severed end and a lumen extending therefrom with a longitudinal axis, the apparatus comprising:
   an insertion device; and
   a plug for insertion along the longitudinal axis into the lumen of the blood vessel, the plug having a distal tip, a tapered outer surface extending from said distal tip, a large diameter section, an interior chamber with a rear opening proximally disposed from said distal tip, a plurality of spokes, and an attachment means, said plurality of spokes extending from said interior chamber and out said rear opening and radially outward, said attachment means disposed within said interior chamber of said plug, for attaching the plug to the insertion device, wherein when the plug is inserted axially into the lumen of the blood vessel adjacent its severed end said plug is sufficiently rigid in order to resist compressive forces applied thereto by the inner wall of the blood vessel such that the plug is gripped by compressive forces exerted by the elastic nature of the inner wall of the blood vessel and said distal tip, said tapered outer surface and said large diameter section together define a continuous occluding surface that occludes blood flow through the lumen of the blood vessel, and
   the insertion device having interface means that cooperates with the attachment means of the plug to attach the plug to the insertion device and means for applying an axial force from a proximal position relative to the rear opening of the plug and the severed end of the blood vessel to insert the plug into the lumen of the blood vessel adjacent its severed end.

2. The apparatus as recited in claim 1 wherein the attachment means of the plug comprises a pilot hole disposed within said interior chamber.

3. The apparatus as recited in claim 1 wherein the plug further comprises an inner corrugated surface disposed within said interior chamber.

4. The apparatus as recited in claim 1 wherein the plug is made of silicon.

5. The apparatus as recited in claim 1 wherein the insertion device further comprises:
   a. a needle;
   b. a tubular needle guard surrounding the needle, the needle fitting into a pilot hole of the plug;
   c. a spring connected to the needle to propel the needle outwards; and
   d. a lever operable to compress and decompress the spring.

6. The apparatus as recited in claim 1 wherein said tapered outer surface defines at least one edge defining said rear opening, and said plurality of spokes extend radially outward at positions offset along said longitudinal axis from said at least one edge.

7. The apparatus as recited in claim 1 wherein said spokes extend radially outward to tips that are spaced apart in an annular fashion at a diameter greater than the cross-sectional diameter of the large diameter section.

8. The apparatus as recited in claim 1 wherein said spokes comprise metal.

9. The apparatus as recited in claim 8 wherein said metal comprises tungsten.

10. A plug for occluding a blood vessel having a severed end and a lumen extending therefrom, and the plug is for use with an insertion device, the plug comprising:
    a distal tip, a tapered outer surface extending from said distal tip, said tapered outer surface having a large diameter section and defining an interior chamber with a rear opening proximally disposed from said distal tip;
    a plurality of spokes that extend from said interior chamber out said rear opening and radially outward, said plug being sufficiently rigid in order to resist compressive forces applied thereto by the inner wall of the blood vessel such that the plug is gripped by compressive forces exerted by the elastic nature of the inner wall of the blood vessel when inserted into the lumen of the blood vessel adjacent its severed end by an insertion device and said distal tip, said tapered outer surface and said large diameter section together define a continuous occluding surface that occludes blood flow through the lumen of the blood vessel; and
    attachment means, disposed within said interior chamber of said plug, for attaching the plug to the insertion device.

11. The plug as recited in claim 10 wherein the attachment means is a pilot hole to enable the plug to be attached to the insertion device.

12. The plug as recited in claim 10 further comprising an inner corrugated surface disposed within said interior chamber.

13. The plug as recited in claim 10 wherein the plug is made of silicone.

14. The plug as recited in claim 10 wherein said tapered outer surface defines a longitudinal axis and includes at least one edge defining said rear opening, and said plurality of spokes extend radially outward at positions offset along said longitudinal axis from said at least one edge.

15. The plug as recited in claim 10 wherein said spokes extend radially outward to tips that are spaced apart in an annular fashion at a diameter greater than the cross-sectional diameter of the large diameter section.

16. The plug as recited in claim 10 wherein said spokes comprise metal.

17. The plug as recited in claim 16 wherein said metal comprises tungsten.

18. A plug for occluding a blood vessel where the plug is for use with an insertion device, comprising:
    a substantially frusto-conical, flexible, non-expanding element having an outer wall with a closed nose, an interior chamber, and a rear opening, said element being sufficiently rigid in order to resist compressive forces applied thereto by the blood vessel such that the plug is gripped by compressive forces exerted by the elastic nature of the blood vessel when inserted into the blood vessel and said distal tip, said tapered outer surface and said large diameter section together define a continuous occluding surface that occludes blood flow through the lumen of the blood vessel;
    a plurality of flexible metal spokes coupled to said element and extending from said interior chamber out said rear opening and in a relaxed state, radially outward and past said non-expanding element; and
    a coupling element disposed within said interior chamber of said plug permitting the plug to be coupled to the insertion device.

19. A plug according to claim 18, wherein:
    said coupling element is integral with said flexible metal spokes.

20. A plug according to claim 19, wherein:
    said coupling element defines a pilot hole which receives the insertion device.

21. A plug according to claim 18, wherein:
    said outer wall has a maximum diameter of between 1 mm and 4 mm.

* * * * *

UNITED STATES PATENT AND TRADEMARK OFFICE
CERTIFICATE OF CORRECTION

| | |
|---|---|
| PATENT NO. | : 7,278,430 B2 |
| APPLICATION NO. | : 10/086753 |
| DATED | : October 9, 2007 |
| INVENTOR(S) | : Sundaram Ravikumar |

It is certified that error appears in the above-identified patent and that said Letters Patent is hereby corrected as shown below:

Title Page, field 12, the inventor's surname "Kumar" is corrected to -- Ravikumar --; field 75, the inventor's complete name "Ravi Kumar" is corrected to -- Sundaram Ravikumar --

Signed and Sealed this

Twenty-fifth Day of December, 2007

JON W. DUDAS
*Director of the United States Patent and Trademark Office*